United States Patent [19]

Christensen et al.

[11] 4,235,920
[45] Nov. 25, 1980

[54] N-ALKYLATED DERIVATIVES OF THIENAMYCIN

[75] Inventors: Burton G. Christensen, Metuchen; Raymond A. Firestone, Fanwood; William J. Leanza, Berkeley Heights, all of N.J.

[73] Assignee: Merck & Co., Inc., Rahway, N.J.

[21] Appl. No.: 861,235

[22] Filed: Dec. 16, 1977

Related U.S. Application Data

[63] Continuation-in-part of Ser. No. 733,611, Oct. 18, 1976, abandoned, which is a continuation-in-part of Ser. No. 634,297, Nov. 21, 1975, abandoned.

[51] Int. Cl.$^3$ .................... C07D 407/04; A61K 31/40
[52] U.S. Cl. ............................ 424/274; 260/245.2 T; 424/250; 424/263; 424/269; 424/270; 424/272; 424/273 R; 542/410; 544/316; 546/272
[58] Field of Search ................... 260/326.31, 245.2 T; 424/274

[56] References Cited

U.S. PATENT DOCUMENTS 3,950,357  4/1976  Kahan et al. .................... 260/326.31

OTHER PUBLICATIONS

C & E News, Sep. 25, 1978, pp. 26–27.

Primary Examiner—Mary C. Lee
Attorney, Agent, or Firm—Frank M. Mahon; Julian S. Levitt; James A. Arno

[57] ABSTRACT

Disclosed are N-alkylated derivatives of the antibiotic thienamycin, which has the following structure:

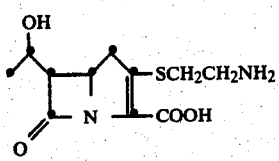

Such compounds and their pharmaceutically acceptable salt, ester and amide derivatives are useful as antibiotics. Also disclosed are processes for the preparation of such derivatives, pharmaceutical compositions comprising such derivatives, and methods of treatment comprising administering such derivatives and compositions when an antibiotic effect is indicated.

8 Claims, No Drawings

N-ALKYLATED DERIVATIVES OF THIENAMYCIN

BACKGROUND OF THE INVENTION

This is a continuation-in-part of co-pending application Ser. No. 733,611, filed Oct. 18, 1976, now abandoned, which in turn is a continuation-in-part of U.S. Ser. No. 634,297, filed Nov. 21, 1975, now abandoned.

This invention relates to certain N-alkyl, N,N-dialkyl, and N,N,N-trialkyl derivatives of the new antibiotic thienamycin. Such compounds and their pharmaceutically acceptable salt, ester and amide derivatives are useful as antibiotics.

This invention also relates to processes for the preparation of such compounds, pharmaceutical compositions comprising such compounds, and methods of treatment comprising administering such compounds and compositions when an antibiotic effect is indicated.

Thienamycin, (I), is disclosed and claimed in co-pending, commonly assigned U.S. patent application Ser. No. 526,992, filed Nov. 25, 1974 (now U.S. Pat. No. 3,950,357, issued Apr. 13, 1976), which patent is incorporated herein by reference since thienamycin may serve as a starting material for the compounds of the present invention:

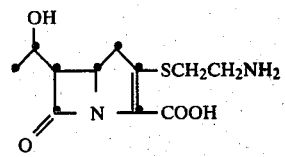

Thienamycin and all of its isomers (in pure form and as mixtures) are also obtainable by the total synthesis disclosed and claimed in co-pending, commonly assigned U.S. patent application Ser. No. 833,210 (Sept. 15, 1977), now abandoned. This application is incorporated herein by reference to the extent that it makes available all isomers of I as starting materials in the preparation of the compounds of the present invention.

Other convenient starting materials for the N-alkylated thienamycin of the present invention are shown below (Ia, Ib, and Ic):

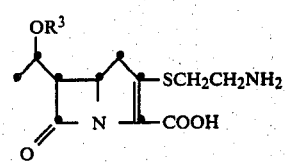

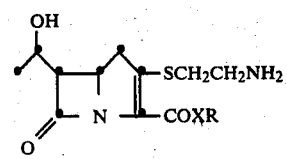

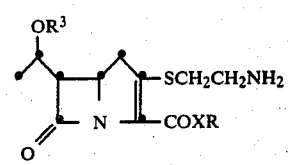

wherein $R^3$, X and R are defined below. Starting materials Ia, Ib and Ic, which are also useful as antibiotics, are disclosed and claimed in co-pending, concurrently filed U.S. patent applications Ser. Nos. 634,006, 634,298, and 634,294, respectively; all filed Nov. 21, 1975, and their corresponding continuation-in-part U.S. patent applications Ser. Nos. 733,655; 733,651; and 733,652; all filed concurrently with the present application and all now abandoned. These applications are incorporated herein by reference since they describe useful starting materials, and processes for converting the N-alkylated thienamycins of the present invention to carboxyl-, O-; and carboxyl- and O-derivatized forms which are also embraced by the present invention and are useful as antibiotics.

The N-alkylated thienamycin derivatives of the present invention may be depicted by the following generic structural formula:

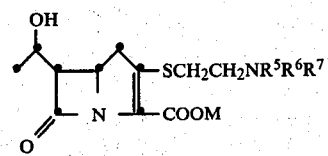

or, more conveniently, by the symbol:

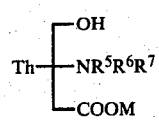

wherein: "Th" symbolizes the bicyclic nucleus of thienamycin and the OH, amino, and carboxyl groups of thienamycin are illustrated; M is H, a salt cation selected from alkali or alkaline earth metals or an amine salt; and $R^5$, $R^6$ and $R^7$ are independently selected from the group consisting of hydrogen (not all of $R^5$, $R^6$ and $R^7$ are hydrogen at the same time) substituted and unsubstituted: lower alkyl having 1–10 carbon atoms, alkenyl having 2–10 carbon atoms, alkynyl having 2–10 carbon atoms, ring substituted and unsubstituted: cycloalkyl, cycloalkenyl, cycloalkenylalkyl, and cycloalkylalkyl having 3–6 ring carbon atoms and 1–6 carbon atoms in the alkyl chain, aryl having 6–10 carbon atoms, aralkyl having 6–10 ring carbon atoms, and 1–6 carbon atoms in the alkyl chain, mono- and bicyclic heteroaryl and heteroaralkyl comprising 4–10 ring atoms one or more of which is selected from oxygen, nitrogen and sulphur and 1–6 carbon atoms in the alkyl chain; and wherein the ring or chain substituent is selected from: halo such as chloro, bromo, iodo and fluoro, azido, cyano, amino, mono-, di and trialkyl substituted amino wherein the alkyl has 1–6 carbon atoms; hydroxyl, alkoxyl having 1–6 carbon atoms; alkylthioalkyl having 1–6 carbon atoms; carboxyl; oxo; alkoxylcarbonyl having 1–6 carbon atoms in the alkoxyl moiety; acyloxy comprising 2–10 carbon atoms; carbamoyl, and mono- and dialkylcarbamoyl wherein the alkyl groups have 1–4 carbon atoms; cyanothio (—SCN); and nitro. It will be recognized that the N,N,N-trialkyl derivatives are quaternary ammonium compounds, the counter ion (anion) of which is not critical and may be selected from halides, such as chloro and bromo, phosphate, sulphate and the like.

The compounds of the present invention also embrace embodiments of the following structure:

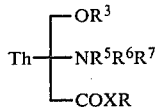

wherein the basic symbolism is as previously defined and X is oxygen, sulphur or NR' (R'=H or R); and R is, inter alia, representatively selected from the group consisting of hydrogen, conventional blocking groups such as trialkylsilyl, acyl and the pharmaceutically acceptable salt, ester and amide moieties known in the bicycli β-lactam antibiotic art; the definition of R is given in great detail below; $R^3$ is (1.) acyl (generically the group $OR^3$ is classifiable as an ester); or (2.) $R^3$ is selected from alkyl, aryl, aralkyl and the like (such that the group $OR^3$ is generically classifiable as an ether). $R^3$ may also be hydrogen. The term "acyl" is be definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl-radicals, and substituted P(III and V) radicals such as substituted phosphorous-, phosphoric-, phosphonous- and phosphonic-radicals, respectively. Such acyl radicals of the present invention are further defined below, as are the radicals (2., above) which constitute the ether embodiments of the present invention.

There is a continuing need for new antibiotics. For, unfortunately, there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as N-alkylated derivatives thereof. These antibiotics are active against a broad range of pathogens which representatively include both gram positive bacteria such as *S. aureus, S. pyogenes* and *B.subtilis* and gram negative bacteria such as *E. coli, Proteus morganii* and Klebsiella. Further objects of this invention are to provide chemical processes for the preparation of such antibiotics and their non-toxic pharmaceutically acceptable salts, pharmaceutical compositions comprising such antibiotics; and to provide methods of treatment comprising administering such antibiotics and compositions when an antibiotic effect is indicated.

DETAILED DESCRIPTION OF THE INVENTION

With respect to the generic description of the present invention (structures II, above) the most preferred embodiments are those wherein $R^5$, $R^6$, and $R^7$ are selected from hydrogen, lower alkyl and alkenyl having from 1 to 6 carbon atoms; such as methyl, ethyl, propyl, allyl and the like; benzyl and nuclear substituted benzyl such as p-t-butyl benzyl and the like; heteroaralkyls such as 4-pyridyl methyl, 2-furyl methyl, 2-thienyl methyl and the like; and $R^3$, X and R are as defined above—especially preferred embodiments are those wherein $R^3$ is hydrogen, X is oxygen and R is hydrogen.

The compounds of the present invention are prepared by reacting thienamycin or a suitable derivative thereof or a suitably protected thienamycin species with an N-alkylating agent. There is no undue criticality in the process of the present invention and any of a variety of well-known N-alkylation procedures may be employed. The identity of the N-alkylating agent is a matter of choice with the limits set by the definition of $R^5$, $R^6$ and $R^7$. The N-alkylation may be conducted in any of a variety of solvent systems which are inert or substantially inert to the desired course of reaction. Suitable solvents include polar solvents such as water, lower alkanoyls such as ethanol, dioxane, tetrahydrofuran (THF), acetonitrile, hexamethylphosphoramide (HMPA), dimethylformamide (DMF) and the like and mixtures (particularly aqueous mixtures) of the above; and non-polar solvents such as benzene and halohydrocarbons such as methylene chloride, chloroform and the like. Typically the reaction is conducted at a temperature of from −40° C. to 50° C. for from 15 minutes to 5 hours. Usually, the reaction is conducted in the presence of an acid acceptor such as propylene oxide, magnesium oxide, potassium carbonate and the like. The preferred N-alkylated agents include active halides, sulfate esters, and Michael addition reagents. The following reagents are representative of such alkylating agents: methyl iodide, allyl bromide, bromo acetone, phenacyl bromide, benzyl bromide, ethylchloroacetate, propargyl bromide, 2-bromoethylethylether, dimethyl sulfate, and methylfluorosulphonate, chloromethylthiocyanate, chloroethylmethylsulfide, bromomethylcyclopropane, 2,4-dinitrofluorobenzene, 2-chloromethylpyridine, acylonitrile, methylmethylacrylate, nitroethylene and the like.

The monoalkyl embodiments of the present invention may be prepared in any of a variety of ways. One convenient starting material is tris-trimethylsilyl thienamycin [Th(TMS)₃]. When it is desired for $R^3$, R or $R^3$ and R to be other than hydrogen, the suitably derivatized starting materials such as Ia, Ib, and Ic (above) may be employed. The reaction is carried out in any of the above-named non-protic solvents in the presence of the N-alkylating agents of choice [R'X', wherein $R'=R^5$, $R^6$ or $R^7$ and X' is halo or sulphate]. The desired product is obtained by aqueous hydrolysis following the N-alkylation step. The following reaction diagram summarizes the process:

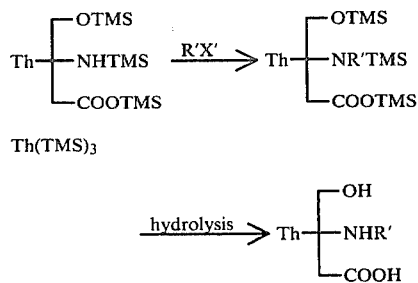

wherein TMS, R' and X' are as defined above.

A second scheme for the preparation of monoalkyl embodiments involves the N-alkylation of an N-substituted thienamycin wherein the substituent is an easily removable, bulky group (R°) such as an aralkyl group, for example substituted and unsubstituted: benzyl, benzylhydryl (—CH(C₆H₅)₂) and trityl (—C(C₆H₅)₃) wherein the ring substituent on the aralkyl is halo, nitro, loweralkyl, loweralkoxyl or the like. The following reaction diagram summarizes this scheme:

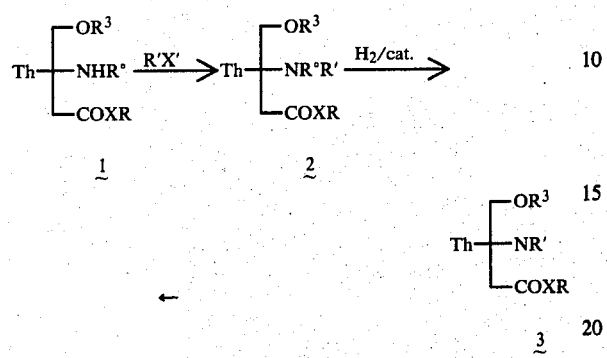

wherein all symbolism is as defined above.

In words relative to the above diagram, starting material 1, prepared for example from the reaction of thienamycin or derivative thereof with an aralkyl halide, is reacted with the N-alkylating agent of choice R'X', as above-described, to provide the N,N-dialkyl intermediate 2. The aralkyl N-substituent R° is readily removable to provide 3 by hydrogenolysis. Suitable conditions for this final cleavage step involve hydrogenating 2 in a solvent such as ethanol under hydrogen (1 to 4 atmospheres) in the presence of a catalyst such as platinum, palladium, or oxides thereof. The ultimate product of this reaction is primarily 3, the N-monoloweralkyl. However, there is some co-presence of N,N-diloweralkyl theinamycin. Such contaminating by-products may be separated by chromatographic methods and the magnitude of contamination may be minimized by employing one equivalent or less of the alkylating agent R'X'.

A third method for the preparation of N-monoalkyl species, particularly N-loweralkyl species, is similar to the above described procedure except that the starting material 1a is N,N-diaralkyl thienamycin. The preparation of such starting materials is described below. The following reaction diagram summarized this process:

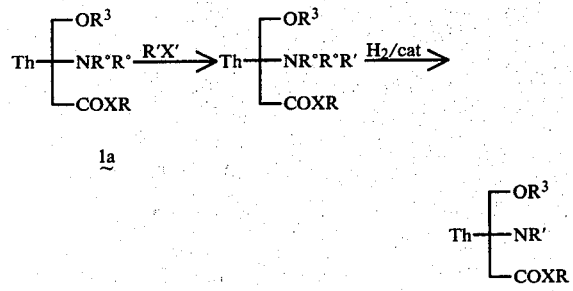

wherein all symbolism is as previously defined. It is to be noted that this scheme for the preparation of N-loweralkyl thienamycins is not complicated by the co-preparation of N,N-diloweralkyl thienamycins.

A fourth method which is particularly suitable for the preparation of N-loweralkyl thienamycins species involves the N-alkylation of a Schiff's Base of thienamycin. The following diagram summarizes the reaction.

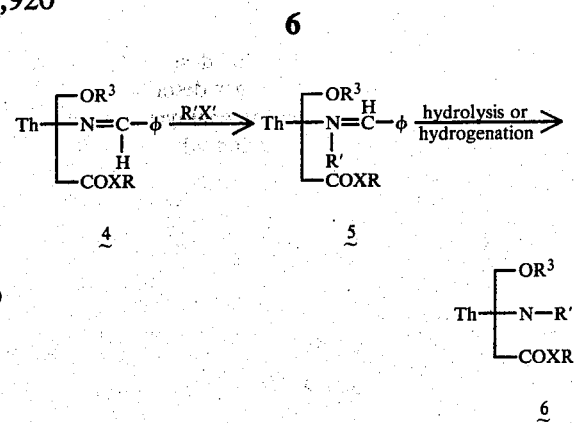

φ = phenyl wherein all symbolism is as previously defined and in addition φ is phenyl, R and R³ may be the trimethylsilyl radical and X may be oxygen. The preferred Schiff's base is that obtained by reacting thienamycin with benzaldehyde or nuclear substituted benzaldehyde. There is no criticality in the process for preparing such Schiff's bases and their preparation is disclosed in copending, commonly assigned U.S. patent application Ser. No. 634,292, and in its continuation-in-part Ser. No. 733,656 filed concurrently with the present application both now abandoned. Such U.S. Patent applications are incorporated herein by reference as they describe the preparation of starting material 4. The reaction of 4 with the alkylating reagent R'X' provides intermediate 5 which upon aqueous hydrolysis or catalytic hydrogenolysis provides the desired N-loweralkyl thienamycin species 6.

A fifth method for preparing N-loweralkyl thienamycins involves the desulfurization of an N-thioacyl thienamycin in the presence of a hydrogenation catalyst such as Raney Nickel:

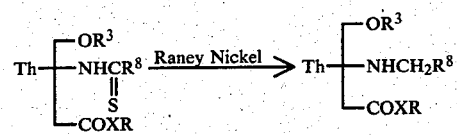

wherein X is oxygen, R³ and R are as previously defined but preferably are hydrogen, and R⁸ is hydrogen, aryl or a lower alkyl moiety having 1-5 carbon atoms. The N-thioacyl thienamycin starting materials are fully disclosed in copending U.S. patent application Ser. No. 634,291 filed Nov. 21, 1975 and in its continuation-in-part U.S. patent application Ser. No. 733,653, both now abandoned, which applications are incorporated herein by reference for their disclosure relative to the preparation of such starting materials. The above desulfurization is typically conducted in polar protic solvents such as water, lower alkanols such as ethanol, and aqueous mixtures thereof at a temperature of from 0°–50° C. for from 30 minutes to 5 hours.

The N,N-dialkyl thienamycin derivatives of the present invention may be prepared in any of a variety of ways. The N-substituents may be the same ("symmetric") or different ("asymmetric"). The symmetrical type may be prepared from starting material 1 when an excess of the alkylating agent is employed. This process gives exclusively the N,N-disubstituted product. Hydrogenation of resulting intermediate to cleave the N- aralkyl substituent provides the desired N,N-dialkyl thienamycin species in the manner described above.

In general, the N,N-dialkyl thienamycin species may be prepared by directed alkylation when the alkylation reaction is conducted in water, a protic solvent or mixtures thereof without protection of the carboxyl group. However when direct alkylation is conducted in an aprotic solvent, such as HMPA, esterification of the free carboxyl group generally occurs. In cases where ester formation is not desired, the carboxyl group is preferably blocked by a conventional, readily removable carboxyl blocking group. [Preparation of such carboxyl blocked thienamycin species is given below.] Further, it should be noted that direct N-alkylation of thienamycin usually provides a mixture of products, the mono-, di-, and trialkyl species. The relative proportions, for steric reasons, of which are determined by the size of R' of the alkylating reagent and the amount of reagent employed. When R' is small (less bulky), such as methyl and ethyl, the N,N,N-trialkyl species predominate. As the size of R' increases, the mono- and dialkyl species predominate.

The symmetrical type may be prepared either by reductive alkylation with an aldehyde (R"CHO, wherein —CH$_2$R"=R$^5$, R$^6$, or R$^7$), or by dialkylation of an ester of thienamycin by an alkyl halide or sulphate followed, if desired, by cleavage of the ester group by standard methods such as hydrogenation.

The asymmetrical types may be prepared by reductive alkylation of a monoalkyl thienamycin species with an appropriate aldehyde, or by alkylating the tris-trimethylsilyl-N-monoalkyl thienamycin with the alkylating agent of choice in the presence of an acid acceptor such as propylene oxide, K$_2$CO$_3$ or MgO. Again, any of the starting materials Ia, Ib, or Ic may be employed to provide the corresponding O-, carboxyl, or O- and carboxyl derivative. The following diagram illustrate the above schemes:

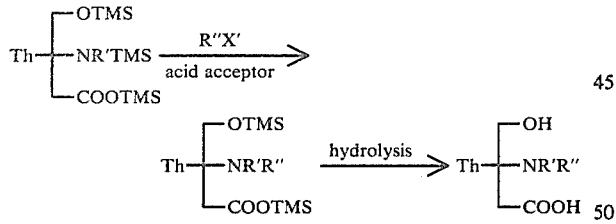

wherein all symbolism has been defined and R' may or may not be the same as R"; R' and R" are selected from R$^5$, R$^6$ and R$^7$;

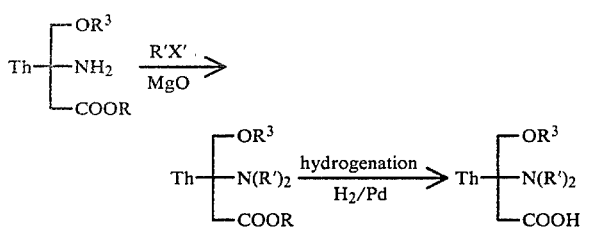

Wherein R is as previously defined and is in the case of the final cleavage an easily removable blocking group such as benzyl or p-nitrobenzyl; R$^3$ is as defined above; R'=R$^5$, R$^6$ or R$^7$;

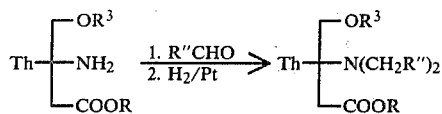

Wherein —CH$_2$R"=R$^5$, R$^6$ or R$^7$; and R and R$^3$ are as defined above.

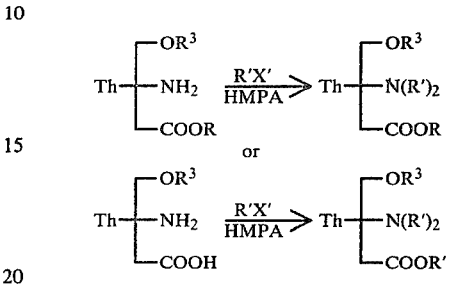

wherein R$^3$ is as defined; R'=R$^5$, R$^6$ or R$^7$; X'=halide or sulphate; and R is as defined—the special case of R=H being illustrated. Again it is to be noted that ester formation may be avoided when operating upon the free acid, when the alkylation is conducted in water or a protic solvent.

N,N,N-trialkyl thienamycin derivatives of the present invention may be prepared from thienamycin, an O-, carboxyl, or O- and carboxyl derivative thereof, or from the N,N-dialkyl species by alkylation with an alkyl halide or sulphate. The carboxyl group may be protected by a conventional blocking group, such as benzyl or p-nitrobenzyl. It is to be noted, however, that R$^3$- and R-substituted N,N-dialkyl thienamycins are suitable substrates when it is desired to prepare compounds of the present invention having the following structure:

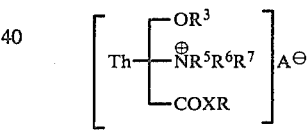

wherein the non-critical counter anion A$^\ominus$ has previously been identified. The following diagram is representative of this final process:

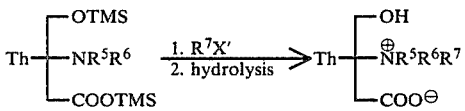

wherein all substituents are as defined above.

Identification of the Radical —COXR

In the generic representation of the compounds of the present invention (II, above), the radical represented by —COXR, is, inter alia, —COOH (X is oxygen and R is hydrogen) and all radicals known to be effective as pharmaceutically acceptable ester, anhydride (R is acyl) and amide radicals in the bicyclic β-lactam antibiotic art, such as the cephalosporins and penicillins and the nuclear analogues thereof.

Suitable radicals (R) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable thienamycin derivatives of the present invention alling in this class are given below. Suitable blocking esters thus include those selected from the following list which is representative and not intended to be an exhaustive list of possible ester groups, wherein X=O and R is given:

(i) R=CR$^a$R$^b$R$^c$ wherein at least one of R$^a$, R$^b$ and R$^c$ is an electron-donor, e.g., p-methoxyphenyl, 2,4,6-trimethylphenyl, 9-anthryl, methoxy, CH$_2$SCH$_3$, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

(ii) R=CR$^a$R$^b$R$^c$ wherein at least one of R$^a$, R$^b$ and R$^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) R=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, t-amyloxycarbonyl, diphenylmethoxycarbonyl and triphenylmethoxycarbonyl.

(iv) R=R$^d$, wherein R$^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

R$^4_3$SiX'; R$^4_2$SiX'$_2$; R$^4_3$Si.NR$^4_2$; R$^4_3$Si.NH.COR$^4$; R$^4_3$Si.NH.CO.NH.SiR$^4_3$; R$^4$NH.CO.NH$^4$.SiR$^4_3$; or R$^4$C(OSiR$^4_3$); HN(SiR$^4_3$)$_2$ wherein X' is a halogen such as chloro or bromo and the various groups R$^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting N-acylated Thienamycin (1) with alcohols, phenols, mercaptans, thiophenols, acylating reagents and the like which yield compounds (2, above) which are then derivatized to establish the R$^3$ group of the compounds of the present invention (II, above). For example, esters and amides of interest are the compounds of the formula II (above) having the following group at the 2-position: —COXR wherein X is oxygen, sulfur, or NR' (R' is H or R), and R is alkyl having 1–10 carbon atoms, straight or branched, such as methyl, ethyl, t-butyl, pentyl, decyl and the like; carbonylmethyl, including phenacyl, p-bromophenacyl, t-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1–10 and preferably 1–6 carbon atoms; but can be branched, straight or cyclic, and the alkyl portion has 1–6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1–6 carbon atoms, e.g., 2,2,2-trichloroethyl, trifluoroethyl, 2-bromopropyl, diiodomethyl, 2-chloroethyl, 2-bromoethyl, and the like; alkenyl having 1–10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1–10 carbon atoms, either straight or branched e.g., 3-pentenyl, propargyl, ethynyl, 3-butyn-1-yl, and the like; alkanoyl, either straight or branched, having 1–10 carbon atoms, such as pivaloyl, acetyl, propionyl, and the like; aralkyl or heteroaralkyl wherein alkyl has 1–3 carbon atoms, and hetero means 1–4 hetero atoms being selected from the group consisting of O, S, or N, such as benzyl, benzhydryl, and substituted benzyl, or benzhydryl, e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1–4 carbon atoms chain); or phthalidyl; or phenylethyl, 2-(p-methylphenyl)ethyl, and the arylthioalkyl analogues, aryloxyalkyl wherein aryl is preferably a phenyl ring ahving 0–3 substituents preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0–3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X is the

group. Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COXR are anhydrides wherein R is benzyloxycarbonyl, ethoxycarbonyl, benzoyl, and pivaloyl.

The most preferred —COXR radicals of the present invention are those wherein (relative to Structure II above) X is oxygen, sulphur or NR' (R' is selected from the group consisting of hydrogen and lower alkyl); and R is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

Identification of R³

In the generic representation of the present invention, structure II (above(, the radical R³ is, in addition to hydrogen, (1.) acyl (generically the group —OR³ is classifiable as an ester); or (2.) R³ is selected from alkyl, aryl, aralkyl, and the like such that the group —OR³ is classifiable as an ether. For the ester embodiments (1) R³ is selected from the following definition of acyl radicals (p=1). In the so-called ether embodiments (2.) of the present invention, R³ is selected from the same acyl radicals wherein the carbonyl moiety,

or more generally

is deleted (p=0); thus R³ is selected from the following radicals wherein all symbolism is defined below:

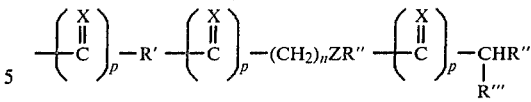

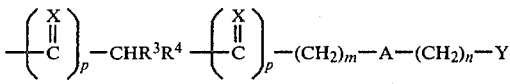

Thus, relative to the definition of R³, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl); alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino -4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)4-isoxazolyl, 4-guanidinomethylphenyl, 4-guanidinomethylbenzyl, 4-guanidinobenzyl, 4- guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, benzamidinomethyl and cyclohexylamidinomethyl.

The acyl group can also be a radical of the formula:

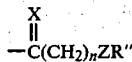
—C(CH$_2$)$_n$ZR'' wherein X is O or S and n is 0-4, Z represents oxygen, sulfur, carbonyl or nitrogen and R'' is defimned as above. Representative members of the substituent —(CH$_2$)$_n$ZR'' that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethylphenyl)thiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

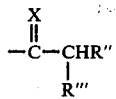

wherein R'' is defined as above and R''' is a radical such as amino, hydroxy, azido, carbamoyl, guanidino, amidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D(—)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl D(—)-2-thienyl-guanidinomethyl, D(—)-α-guanidinobenzyl α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl-)aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobnzyl, α-phosphononbenzyl, α-diethylphosphono, and α-monoethylphosphono. Further acyl radicals of interest in this class when X=oxygen are:

—CCHR$^3$R$^4$ wherein R$^3$ and R$^4$ are as defined below. R$^3$ represents hydrogen, halo, such as chloro, fluoro, bromo, iodo, amino, guanidino, phosphono, hydroxy, tetrazolyl, carboxy, sulfo, or sulfamino and R$^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substituted heterocycles, phenylthio, phenyloxy lower alkyl of 1-6 carbon atoms, heterocyclic or substituted heterocyclic thio groups; or cyano. The substituents on the moieties, R$^3$ and R$^4$, can be halo, carboxymethyl, guanidino, guanidinomethyl, carboxamidomethyl, aminomethyl, nitro, methoxy or methyl. When R$^3$ is selected from the group consisting of hydrogen, hydroxy, amino or carboxy and R$^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl- 1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-theinylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorous (2) radicals:

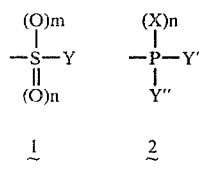

wherein with respect to 1, m and n are integers selected from 0 or 1 and Y=O⊖M⊕, —N(R″)₂, and R″; wherein M⊕ is selected from hydrogen, alkali metal cations and organic bases; and R″ is as defined above, e.g., alkyl, alkenyl, aryl and heteroaryl. With respect to 2 X=O or S; n=0 or 1; and Y′ and Y″ are selected from the group consisting of O⊖M⊕, —N(R″)₂, R″ and ZR″ wherein all symbolism is as defined above, e.g., R″ and ZR″ are representatively: alkyl, alkenyl, aryl, heteroaryloxy, Y′ and Y″, including R″ moieties, can be joined together to form cyclic ester, ester-amide and amide functions. Illustrative examples of 1 are O-(methylsulphonyl)theinamycin, O-(p-nitrophenylsulphonyl)thienamycin, O-(p-chlorophenylsulphinyl)thienamycin, O-(o-nitrophenylsulphenyl)thienamycin, O-sulfamoylthienamycin, O-dimethylsulphamoylthienamycin and thienamycin O-sulphonic acid sodium salt. Illustrative examples of 2 are O-(dimethoxyphosphino)thienamycin, O-(dibenzyloxyphosphino)theinamycin, O-(dihydroxyphosphino)thienamycin disodium salt, O-(dimethoxyphosphinyl)thienamycin, O-(dimethoxyphosphinothioyl)thienamycin, O-(dibenzyloxyphosphinyl)thienamycin, and O-(dihydroxyphosphinyl)thienamycin disodium salt.

An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkyl silyl, for example, trimethylsilyl and t-butyldimethylsilyl are also of interest.

The following radicals, according to the foregoing definition of acyl, are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanidinoacetyl, 3-guanidinopropionyl, N³-methylguanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, N³-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl, sulfo, phosphono,

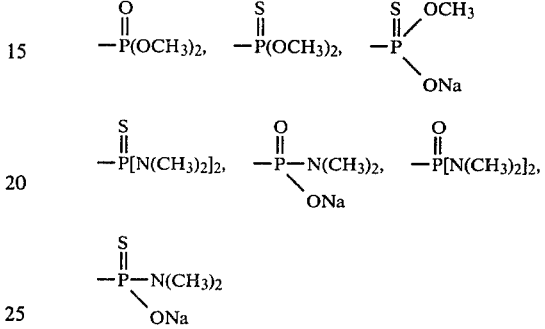

An especially preferred class of acyl radicals are terminally substituted acyls wherein the substituent is a basic group such as substituted and unsubstituted: amino, amidino, guanidino, guanyl and nitrogen-containing mono- and bicyclic heterocyles (aromatic and non-aromatic) wherein the hetero atom or atoms, in addition to nitrogen, are selected from oxygen and sulphur. Such preferred substituted acyls may be represented by the following formula:

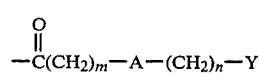

wherein m, and n are integers selected from 0 to 5; A is O, NR′ (R′ is hydrogen or loweralkyl having 1–6 carbon atoms), S or A represents a single bond; and Y is selected from the following group:

(1) amino or substituted amino:

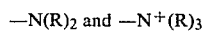

wherein the values for R are independently selected from: hydrogen; N(R′)₂ (R′ is hydrogen or loweralkyl having 1–6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2–6 carbon atoms; cycloalkyl and cycloalkylalkyl wherein the cycloalkyl moiety comprises 3–6 carbon atoms and the alkyl moiety comprises 1–3 carbon atoms, two R groups may be joined together with the N atom to which they are attached to form a ring having 3–6 atoms.

(2) amidino and substituted amidino:

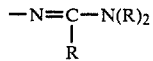

wherein the value of R is independently selected from the group consisting of: hydrogen; N(R′)₂ (R′ is hydrogen or loweralkyl having 1–6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3) guanidino and substituted guanidino:

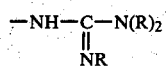

wherein R is as defined in 2. (above).

(4) guanyl and substituted guanyl:

wherein R is as defined in 2. (above).

(5) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1-6 carbon atoms):

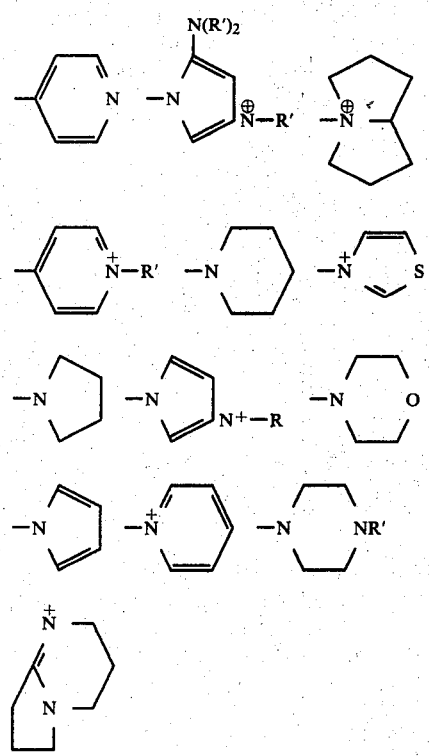

The following specific acyl radicals falling within this class are additionally representative and are preferred:

-continued

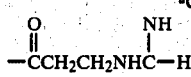
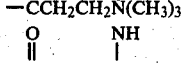
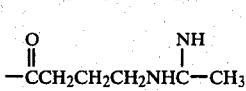
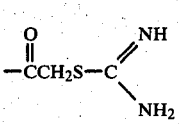
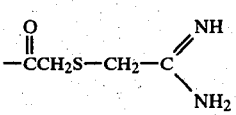
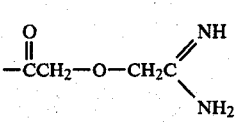

However, it is to be understood that any acyl radical may be employed in the practice of the invention and is to be considered within the scope of the invention.

Preparation of Starting Materials Ia, Ib, and Ic

The above-described starting materials are conveniently prepared from an N-protected thienamycin (1), such as an N-acylated thienamycin (1).

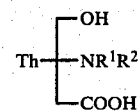

wherein $R^1$ and $R^2$ are selected from hydrogen and the above-defined acyl radicals. Preferably $R^1$ is hydrogen and $R^2$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are the substituted and unsubstituted carbobenzyloxy radical:

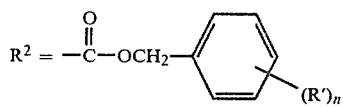

wherein n is 0-2 (n=0, R'=hydrogen) and R' is lower alkoxy or nitro; and bromo-t-butoxycarbonyl.

The ultimate N-deblocking procedure for the preparation of Ia, Ib or Ic is accomplished by any of a variety of well known procedures which include hydrolysis or hydrogenation; when hydrogenation is employed suitable conditions involve a solvent such as a loweralkanoyl in the presence of a hydrogenation catalyst such as palladium, platinum or oxides thereof.

The N-acylated intermediate (1, above) is prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester.

Such N-acylated thienamycin starting materials are fully described in co-pending, concurrently filed U.S. patent application Ser. No. 634,291 filed Nov. 21, 1975 and in its continuation-in-part U.S. patent application Ser. No. 733,653 filed concurrently with the present application both now abandoned. These applications are incorporated herein by reference.

The acylation reaction may be conducted at a temperature in the range of from about −20° to about 100° C., but is preferably conducted at a temperature in the range of from −9° C. to 25° C. Any solvent in which the reactants are soluble and substantially inert may be employed, for example polar solvents such as water, alcohols and polar organic solvents in general such as dimethylformamide (DMF), hexamethyl, phsophoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

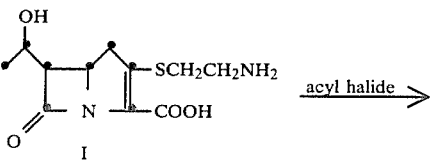

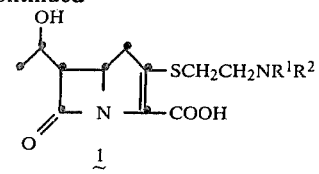

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceeds rapidly to give the tris-triorganosilyl derivative, for example tris-trimethylsilyl thienamycin $Th(TMS)_3$:

Such derivatives, which are readily soluble in organic solvents, are conveniently prepared by treating thienamycin with an excess of hexamethyldisilazane and a stoichiometric amount of trimethylchlorosilane at 25° C., with vigorous stirring under a $N_2$ atmosphere. The resulting $NH_4Cl$ is removed by centrifugation and the solvent is removed by evaporation to provide the desired silyl derivative.

The intermediate starting materials Ib are prepared according to the following scheme; however, it should be noted that direct esterification, without protection of the amino group, is also possible.

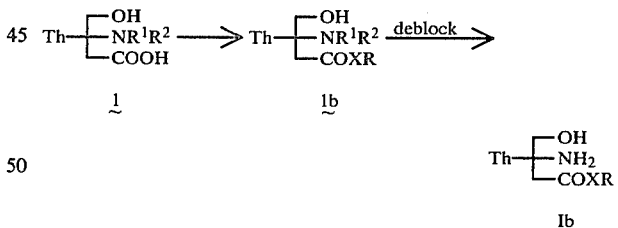

wherein all symbolism is as previously defined.

In general, the transformation (1→Ib) is accomplished by conventional procedures known in the art. Such procedures include:

(1) Reaction of 1 (or I) with a diazoalkane such as diazomethane, phenyldiazomethane, diphenyldiazomethane, and the like, in a solvent such as dioxane, ethylacetate, acetonitrile and the like at a temperature of from 0° C. to reflux for from a few minutes to 2 hours.

(2) Reaction of an alkali metal salt of 1 with an activated alkyl halide such as methyliodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

(3) Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C. to reflux for from 15 minutes to 18 hours, include CHCl$_3$, CH$_3$Cl, CH$_2$Cl$_2$ and the like.

(4) Reaction of an N-acylated acid anhydride of 1 prepared by reacting the free acid 1 with an acid chloride such as ethylchloroformate, benzylchloroformate and the like, with an alcohol such as those listed in (3) under the same conditions of reaction as given above for (3). The anhydride is prepared by reacting 1 and the acid chloride in a solvent such as tetrahydrofuran (THF), CH$_2$Cl$_2$ and the like at a temperature of from 25° C., to reflux for from 15 minutes to 10 hours.

(5) Reaction of labile esters of 1 such as the trimethylsilyl ester, dimethyl-t-butylsilyl ester or the like with RX' wherein X' is halogen such as bromo and chloro and R is as defined, in a solvent such as THF, CH$_2$Cl$_2$ and the like at a temperature of from 0° C. to reflux for from 15 minutes to 16 hours. For example according to the following scheme:

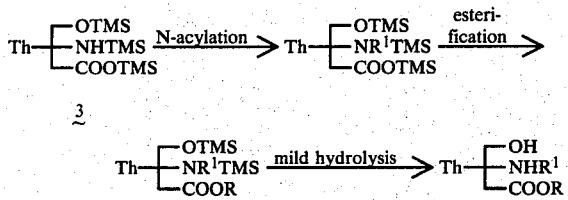

wherein TMS is triorganosilyl such as trimethylsilyl and all other symbolism is as previously defined.

The amides of the present invention are most conveniently prepared by reacting the acid anhydride of Ib (X=O, R=acyl) with ammonia or with the amine of choice, e.g., the alkyl-, dialkyl-, aralkyl- or heterocyclic amines listed above.

The above-recited schemes of esterification are well known in the related bicyclic β-lactam antibiotic art and indeed in all of general organic synthesis and it is to be noted that there is no undue criticality of reaction parameters in the preparation of the N-acylated, carboxyl derivatives Ib useful as starting materials in the practice of the present invention.

Starting materials Ia and Ic are conveniently prepared by any of a variety of well-known esterification or etherification reactions upon the secondary alcoholic group of 1b. Such procedures include:

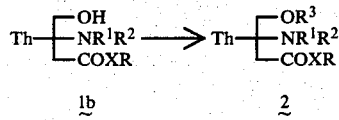

(1) For the preparation of ether embodiments of the present invention, the acid catalized reaction of 1b with a diazoalkane such as diazomethane, phenyldiazomethane, diphenyldiazomethane and the like in an inert solvent such as dioxane, tetrahydrofuran (THF), halohydrocarbons such as CH$_2$Cl$_2$, ethylacetate and the like in the presence of a catalytic amount of a strong acid or Lewis acid such as toluenesulfonic acid, trifluoroacetic acid, fluoboric acid, boron trifluoride and the like at a temperature of from −78° C. to 25° C. for from a few minutes to 2 hours.

(2) For the preparation of ether embodiments of the present invention, the reaction of 1b with an alkylating agent such as active halides, for example methyliodide, benzylbromide, m-phenoxybenzylbromide and the like; alkylsulphonates such as dimethylsulphate, diethylsulphate, methylfluorosulphonate and the like in the presence of a strong base capable of forming the alcoholate anion of 1b. Suitable bases include alkali and alkaline earth metal oxides and hydrous oxides, alkali metal alkoxides such as potassium, tertiarybutoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from −78° C. to 25° C., for from a few minutes to 4 hours.

(3) For the preparation of ester embodiments, of the present invention, the reaction of 1b with any of the above-listed acyl radicals in their acid form. This reaction may be conducted in the presence of a carbodiimide condensing agent such as dicyclohexylcarbodiimide or the like. Suitable solvents include any inert solvent such as CHCl$_3$, CH$_2$Cl$_2$, DMF, HMPA, acetone, dioxane and the like at a temperature of from 0° C. to 60° C. for from 15 minutes to 12 hours.

(4) For the preparation of ester embodiments of the present invention, the reaction of 1b with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as NaHCO$_3$, MgO, triethylene, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl, ethyl carbonic anhydride, methylchloroformate, bis(p-nitrobenzoyl)phosphorochloridate and the like.

(5) For the preparation of ester embodiments of the present invention, the reaction of 1b with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from −70° C. to 60° C. for from 15 minutes to 18 hours.

The intermediate 2 is then N-deblocked as described above to provide starting material Ic. From Ic, Ia is prepared by deblocking the carboxyl group:

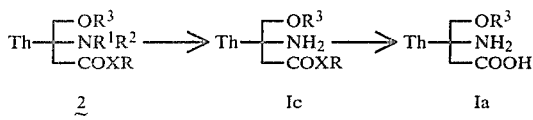

Starting material Ia is conveniently and preferably obtained when X is oxygen and R is a readily removable carboxyl protecting or blocking group (see above). Starting material Ia is prepared by deblocking according to any of a variety of well known procedures which include hydrolysis and hydrogenation. When the preferred carboxyl-blocking groups are employed (below), the preferred deblocking procedure is hydrogenation, wherein the intermediate species (Ic or 2) in a solvent such as a lower alkanoyl, is hydrogenated in the presence of a hydrogenation catalyst such as palladium, platinum or oxides thereof.

In this connection, it is noted that suitable "blocking groups" R include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" R include benzyl, phenacyl, n-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

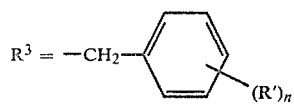

wherein n is 0–2 (n=O, R'=H) and R' is loweralkoxyl or nitro.

In the alternative it should be noted that the compounds of the present invention may be arrived at by operating upon the N-alkylated thienamycin to achieve derivatization by establishment of $R^3$ and/or —COXR. Such procedure is exactly as described above except that the N-alkylated species replaces the N-acylated species and, of course, there is no need to N-deblock.

The products of this invention (II) form a wide variety of pharmacologically acceptable salts with inorganic and organic bases; these include, for example, metal salts derived from alkali or alkaline earth metal hydroxides, carbonates or bicarbonates and salts derived from primary, secondary or tertiray amines such as monoalkylamines, dialkylamines, trialkylamines, lower alkanolamines, di-loweralkanolamines, lower alkylenediamines, N,N-diaralkyl lower alkylenediamines, aralkylamines, amino substitued lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g, with hydrochloric hydrobromic, sulfuric, nitric, toluene-p-sulphonic and methane sulphonic acids may also be employed, in such instances where the acyl radical contains a basic group.

The salts can be mono-salts such as the monosodium salt obtained by treating one equivalent of sodium hydroxide with one equivalent of the product (II), also mixed di-salts. Such salts may be obtained by treating one equivalent of a base having a divalent cation such as calcium hydroxide, with one equivalent of the product (II). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel thienamycin derivatives of the present invention are valuable antimicrobial substances which are active against various gram-positive and gram-negative pathogens such as *Bacillus subtilis, Salmonella schottmuelleri* and *Proteus vulgaris.* Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa,* Pseudomonas and *Bacterium proteus.* The antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycoo, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention.

EXAMPLE 1

Preparation of N,N-di-p-t-Butylbenzyl-Thienamycin-p-t-butylbenzyl Ester

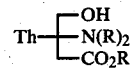
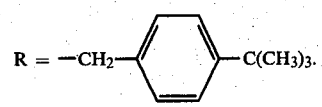

Thienamycin, 40 mg., is stirred 3½ hours in 0.6 ml. HMPA with 0.0275 ml. p-t-butylbenzyl bromide. The Thienamycin goes into solution within 30 min. The reaction mixture is diluted with ethylacetate (EtOAc), and washed successively with aqueous $K_2HPO_4$, water (2x) and brine. The EtOAc layer is dried with $MgSO_4$, filtered and evaporated. The residue is chromatographed by TLC on silica gel, eluting with 5% MeOH in $CHCl_3$. Pure title compound, 4 mg., is obtained at Rf ca. 0.6. IR ($\mu$, film): 3.0, OH; 5.62, $\beta$-lactam; 5.90, ester, NMR ($\delta CDCl_3$): 1.29 (s, t-Bu), 2.6–3.3 (m, $CH_2$'s), 3.57 (s, $NCH_2$), 3.8–4.4 (m, $\beta$-lactam CH's), 5.23 (s, $OCH_2$), 7.29 (s, aryl). MS: m/e 710, 666,624, 367, 335, 322.

Following the above procedure except substituting for p-t-butylbenzyl bromide an equivalent amount of p-methoxybenzylbromide, there is obtained N,N-Bis-p-methoxybenzyl Thienamycin p-methoxybenzyl ester.

EXAMPLE 2

N-p-nitrobenzyl thienamycin p-nitrobenzyl ester and N,N-bis p-nitrobenzyl thienamycin p-nitrobenzyl ester To a solution of thienamycin (71 mg.) in 2 ml of dimethylsulfoxide is added a solution of 27 mg of triethylamine in 0.27 ml of methylene chloride followed by 56 mg of p-nitrobenzyl bromide. The mixture is stirred for ½ hour at 25° C., then 7 ml of methylene chloride and 7 ml of 0.1 N pH 9 buffer are added. The organic phae is separated, washed with water and with brine and then evaporated. The residue is chromatographed on a 1,000$\mu$ 8"×8" silica plate developed with ethylacetate. The band at 0.5-2.5 cm is extracted with ethylacetate yielding N-p-nitrobenzyl thienamycin p-nitrobenzyl ester in UV$\lambda_{max}$ 267 m$\mu$ Sh 320 m$\mu$, relative absorbance 3:2. The band at 4.5-7 cm yields N,N-bis-p-nitrobenzyl thienamycin p-nitrobenzyl ester. UV$\lambda_{max}$ 267 m$\mu$ Sh 320 m$\mu$. Relative absorbance 2:1.

EXAMPLE 3

Preparation of N,N-Dimethyl Thienamycin

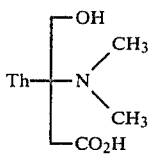

Thienamycin (12.7 mg) is dissolved in 2 ml of an aqueous formaldehyde solution (0.07%) and hydrogenated at 40 psi using platinum oxide (14 mg) catalyst. After four hours, the solution is adjusted to pH 7.0 and chromatographed on a column of XAD-2 resin (15 ml.). The column is eluted with water. A fraction is collected containing a mixture of thienamycin and N,N-dimethyl thienamycin. Analytical high pressure liquid chromatography on $C_{18}$ Porasil with 10% tetrahydrofuran in water as solvent shows two peaks with retention times of 1.75 and 2.5 minutes.

EXAMPLE 4

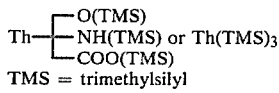

TMS = trimethylsilyl

Preparation of Silylated-Thienamycin

Thienamycin (80.0 mg.) is suspended in 40 ml. tetrahydrofuran (THF) under a $N_2$ atmosphere and is concentrated to 10 ml., hexamethyldisilazane (1.0 ml.) and trimethylchlorosilane (300 μl) is added. The mixture is reacted for 20 mins. at 25° C., with vigorous stirring. The suspension is then centrifuged to remove ammonium chloride. The supernatant is evaporated to an oil under a nitrogen stream for future reaction.

EXAMPLE 5

Preparation of N-Methyl Thienamycin

Th(TMS)$_3$, prepared from 20 mg. of Thienamycin is dissolved 1 ml. of tetrahydrofuran. Dimethylsulfate (15 mg.) is added and the mixture is stirred at 23° C. for 2 hours. Phosphate buffer (pH 7, 1 ml) is added and the mixture adjusted to pH 4 and stirred for 15 minutes. The mixture is adjusted to pH 7 and extracted with ethyl acetate. The aqueous layer is separated and applied to a column (40 ml.) of XAD-2 resin. The column is eluted with water and the effluent is monitored by refractive index and U.V. absorbance; initial fractions containing inorganic salts are discarded; the portions containing N-methyl thienamycin are evaporated to a small volume and freeze-dried.

EXAMPLE 6

N-Methyl Thienamycin

A mixture of thienamycin (272 mg) and trimethylsilyl imidazolyl (280 mg) in 20 ml of THF is stirred at 25° C., for 30 minutes. p-Nitrobenzaldehyde (120 mg.) and powdered anhydrous magnesium sulfate (0.5 g) are added and the solution is evaporated under reduced pressure to 2 ml. The solution is stirred at 25° C., for 4 hours. To the resulting solution of O-trimethylsilyl N-p-nitrobenzylidene thienamycin trimethylsilyl ester is added 150 mg of dimethyl sulfate and the mixture is stirred at 25° C., for one hour. The mixture is poured into 10 ml of 0.1 N pH 6 phosphate buffer and after stirring for 15 minutes, extracted with ether. The aqueous phase is chromatographed on 200 g of XAD-2 resin. Elution with water yields a fraction containing N-methyl thienamycin which is concentrated and freeze-dried.

EXAMPLE 7

Preparation of Thienamycin Benzyl Ester

Step A: N-(p-Nitrobenzyloxycarbonyl)-Thienamycin Sodium Salt

To thienamycin (43 mg.) at 0° C., is added 10 ml. 1:1 tetrahydrofuran (THF):Water. The mixture is rapidly stirred while 102 mg. NaHCO$_3$ (10 equivalent) is added, and then, dropwise with stirring over 2 minutes, four equivalents of o-nitrobenzylchloroformate is added. After 30 minutes, the pH is adjusted to 7 with aqueous 25% H$_3$PO$_4$ and the solution extracted 3X with ether. The aqueous portion is adjusted to pH 2.2 at 0° C.; 500 mg. solid NaCl is added. The cold acidic solution is extracted 3X with cold EtOAc. The EtOAc extracts are combined and quickly backwashed with cold brine; dried with MgSO$_4$, filtered and back-extracted with 10 ml of water containing 1.75 equivalents of solid NaHCO$_3$. The extract is lyophilized in vacuo at 20° C. to provide the title compound.

Step B: N-(p-Nitrobenzyloxycarbonyl)-Thienamycin Benzyl Ester

The product of Step A in 7.5 ml EtOAc is treated with an excess of phenyldiazomethane (4 ml. of a solution comprising 20 mg/ml. ether) at 4° C. for 2 hours. The mixture is concentrated to wet residue at 20° C. under reduced pressure. The desired compound is isolated by thin layer chromatography, eluting with EtOAc; ether (9:1) to afford 17.5 mg. of N-(p-nitrobenzyloxycarbonyl)-thienamycin benzyl ester.

Step C: Thienamycin Benzyl Ester

The compound of Step B is dissolved in ethyl alcohol, 35 mg. PtO$_2$ is added and hydrogenated at 50 lbs. pressure for 45 min. The reaction mixture is centrifuged, liquid decanted and evaporated, and subjected to preparative thin layer chromatography on silica gel, eluting with 1:4 methanol:CHCl$_3$.

EXAMPLE 8

Preparation of N,N-Dimethyl Thienamycin

A mixture of thienamycin benzyl ester (18 mg.), methyl iodide (14 mg.) and MgO (4 mg.) in 2 ml. of hexamethyl phosphoramide is stirred at 25° C. for one hour. The mixture is poured into hexane yielding a precipitate of crude N,N-dimethyl thienamycin benzyl ester which is taken up in ethyl acetate and purified by thin layer chromatography on silica gel.

A solution of 10 mg. of N,N-dimethyl thienamycin benzyl ester in 1 ml. of dioxane-water, 4:1, is hydrogenated at 40 psi in the presence of 10 mg. of palladium oxide for 2 hours. The catalyst is removed by filtration and the filtrate is shaken with a mixture of 5 ml. of ethyl acetate and 5 ml. of 0.01 N, pH 7 phosphate buffer. The aqueous phase is separated, evaporated to a small volume and freeze-dried, yielding N,N-dimethyl thienamycin.

EXAMPLE 9

N-Benzyl and N,N-Dibenzyl Thienamycin

A mixture of thienamycin (150 mg) benzyl bromide (300 ml) and sodium bicarbonate (200 mg) in 10 ml of 80% aqueous ethanol is stirred at 23° for 5 hours. The solution is evaporated under reduced pressure to 2 ml, diluted with 5 ml of water and extracted with ether. The aqueous layer is chromatographed on a column of 100 ml of XAD-2 resin. Elution with water removes unreacted thienamycin. Elution with increasing concentrations of tetrahydrofuran (THF) gives a fraction containing N-benzyl thienamycin followed by a fraction containing N,N-dibenzyl thienamycin which are recovered by lyophilization.

Following the above procedure but substituting for the benzyl bromide an equivalent amount of allyl bromide there are obtained N-allyl and N,N-diallyl thienamycin.

EXAMPLE 10

N-Ethyl-N,N-bis-p-methoxybenzyl thienamycin, p-methoxybenzyl, ester Iodide

A solution of 100 mg of N,N-bis-p-methoxybenzyl thienamycin p-methoxybenzyl ester and 0.5 ml of ethyl iodide in 1 ml of dimethylformamide (DMF) is stirred at 25° C. for 2 hours. The excess reagents and solvent are removed under reduced pressure and the residue is triturated with ether to give the solide product.

EXAMPLE 11

N-Ethyl thienamycin

A solution of 120 mg of N-ethyl-N,N-bis-p-methoxybenzyl thienamycin, p-methoxyethyl ester Iodide in 5 ml of 80% aqueous ethanol containing 20 mg of sodium bicarbonate is hydrogenated in the presence of 100 mg of palladium oxice at 40 psig for 4 hours at 25° C. The catalyst is removed by filtration and the filtrate is evaporated to 2 ml, diluted with 5 ml of water and extracted with ether. The aqueous phase is chromatographed on 100 ml of XAD-2 resin. Elution with water yields N-ethyl thienamycin which is recovered by lyophilization.

EXAMPLE 12

N,N-Dimethyl N-Benzyl Thienamycin

A solution of N-benzyl thienamycin (200 mg) in 5 ml of 50% aqueous dioxane is titrated to pH 8.4. Dimethyl sulfate (0.5 ml) in 2 ml of dioxane is added with stirring during 10 minutes. The pH is maintained at 8.4 by the addition of 1.0 N sodium hydroxide by means of an automatic titrator. The mixture is stirred an additional hour then diluted with 10 ml of water, adjusted to pH 7 and extracted with ether. The aqueous phase is concentrated to 5 ml and chromatographed on 200 ml of XAD-2 resin. The column is eluted with water followed by 20% aqueous THF. The N,N-dimethyl N-benzyl thienamycin is recovered from the THF eluate by lyophilization.

EXAMPLE 13

N,N-Dimethyl Thienamycin

A solution of N,N-dimethyl N-benzyl thienamycin is hydrogenated following the procedure of Example 11 yielding N,N-dimethyl thienamycin.

EXAMPLE 14

N-Salicyclidene Thienamycin benzyl ester

Thienamycin (115 mg) is dissolved in 4 ml of 50% aqueous dioxane. The solution is cooled to 0° C. and titrated to pH 5 with N sulfuric acid. Phenyldiazomethane 60 mg in 0.9 ml of dioxane is added during 5 minutes with vigorous stirring while the pH is maintained at 5-5.5 under control of a pH state. After reacting an additional 5 minutes the mixture is extracted with ether. The aqueous layer is adjusted to pH 8.3 with sodium bicarbonate solution and extracted with ethyl acetate. To the solution containing thienamycin benzyl ester is added 35 μl of salicyladehyde and anhydrous magnesium sulfate. The solution is concentrated to 1 ml on the rotary evaporator and allowed to stand at 25° C. for one hour. The course of the reaction is followed by TLC on silica gel in 20% methanol-chloroform. A new spot at Rf 0.8 appears. The product is isolated by preparative TLC in 50% ethylacetate-chloroform and appears as a yellow band at Rf 0.32; U.V. $\lambda_{max}$ 259 mμ and 322 mμ of equal intensity. d(CH$_3$CHOH); 6.7–7 and 5.7–6.4 (multiplets); 4.72, s, (OC$\underline{H}_2$); 2.5–7.5 (multiplex aromatic H) and 1.75, $$S, (C=N)$$
$$H$$

Following the above procedure but substituting diphenyl diazomethane for phenyldiazomethane there is obtained salicylidene thienamycin benzhydryl ester NMR 8.67

$$H$$
$$d(CH_3COH)$$

5.65–7.1 (aliphatic multiplex); 2.5–3.2 (aromatic multiplex)

$$1.67 (C=N)$$
$$H$$

Following the above procedure but substituting p-nitro benzaldehyde for salicyaldehyde there is obtained p-nitrobenzylidene thienamycin benzyl ester and the corresponding benzhydryl ester. TLC 5:1 CHCl$_3$ EtOH Rf 0.8. Similarly, when benzaldehyde, p-bromobenzaldehyde, p-dimethylaminobenzaldehyde, 5,5-dimethyl-1,3-cyclohexanedione, dimethylaminoacetaldehyde, and isobutyraldehyde are substituted for salicyaldehyde the corresponding benzhydryl and benzyl esters are obtained.

EXAMPLE 15

N-Ethyl N-p-bromobenzylidene thienamycin benzyl ester Ethylsulfate p-Bromobenzylidene thienamycin benzyl ester (200 mg) is dissolved in 2 ml of methylene chloride and 0.2 ml of diethyl sulfate is added. The solution is stirred at 40° for 5 hours; 20 ml of ether is added and the precipitate, N-ethyl-N-p-bromobenzylidene thienamycin benzyl ester ethylsulfate, is recovered by filtration.

EXAMPLE 16

N-Ethyl Thienamycin

A solution of N-ethyl-N-p-bromobenzylidene thienamycin Ethylsulfate (200 mg) in 5 ml of 80% ethanol containing 40 mg of sodium bicarbonate is hydrogenated in the presence of 0.2 g of palladium oxide at 40 psig for 4 hours. The catalyst is removed by filtration. The filtrate is evaporated to 2 ml, diluted with 5 ml of water and extracted with ether. The aqueous phase is chromatographed on 200 ml of XAD-2 resin. The column is eluted with water and the fractions containing N-ethyl thienamycin are lyophilized.

EXAMPLE 17

N-Methylthienamycin Benzyl Ester

A solution of N-methylthienamycin (50 mg) in 1 ml of water and 1 ml of dioxane is cooled, to 0° and adjusted to pH 5 with N sulfuric acid. Phenyldiazomethane, (37 mg) in 0.5 ml of dioxane is added during 5 minutes while the pH is maintained at 5 to 5.5 by means of an automatic titrator. The mixture is diluted with water (5 ml) and extracted with ether. The aqueous phase is overlayered with ethylacetate, cooled and adjusted to pH 2.5. The ethylacetate is separated by centrifugation and the aqueous phase is adjusted to pH 8.0 with sodium bicarbonate and extracted twice with ethylacetate. The extracts are combined and evaporated and the product is isolated by preparative thin layer chromatography on silica gel using 5:1 chloroform-methanol solvent.

Following the above procedure but starting with N,N-dimethyl thienamycin, there is obtained N,N-dimethyl thienamycin benzyl ester.

EXAMPLE 18

N-o-Hydroxybenzyl Thienamycin Benzyl Ester

A solution of N-salicylidene thienamycin benzyl ester (40 mg) in 1 ml of dioxane is hydrogenated at 40 psig and 23° C. in the presence of 10 mg of platinum oxide for 2 hours. The catalyst is removed by filtration and the filtrate is evaporated. The residue is taken up in chloroform and chromatographed on silica gel affording essentially pure N-orthohydroxybenzyl thienamycin benzyl ester.

Following the above procedure except replacing the N-salicylidene thienamycin benzyl ester with an equivalent amount of: N-benzylidene thienamycin benzyl ester, N-p-bromobenzylidene thienamycin benzyl ester, N-dimethylaminobenzylidene thienamycin benzyl ester, N-dimethylaminoethylidene thienamycin benzyl ester, and N-2-methylpropylidene thienamycin benzyl ester, there is obtained, respectively: N-benzyl thienamycin benzyl ester, N-p-bromobenzyl thienamycin benzyl ester, N-p-dimethylaminobenzyl thienamycin benzyl ester, N-dimethylaminoethyl thienamycin benzyl ester, and N-isobutyl thienamycin benzyl ester.

EXAMPLE 19

N,N,N-Trimethyl Thienamycin

A solution of Thienamcyin (150 mg) in 7.5 ml of 0.1 N pH 7 phosphate buffer and 7.5 ml of dioxane is adjusted to pH 8.4. Dimethylsulfate (1 ml) is added and the solution is rapidly stirred for 40 minutes while the pH is maintained at 8.4 by the addition of N sodium hydroxide solution. The solution is extracted twice with ether. The aqueous phase is evaporated to 4 ml and applied to a column (200 ml) of XAD-2 resin. The column is eluted with water and the progress of the separation is followed by high pressure liquid chromatography on $C^{18}$ Bondapak resin using 10% aqueous acetonitrile. The retention time of the product is 1.2 x thienamycin. The fractions containing the product are combined, concentrated and freeze dried giving 41 mg of N,N,N-trimethyl thienamycin. Electrophoresis (50 V/cm, 2 hrs, pH 7 buffer) shows a bioactive zone which moves 6 cm towards the cathode. The NMR spectrum (60 MHZ, $D_2O$) shows a strong methyl singlet at 6.78 $\tau$ with an integral 3X the side chain methyl doublet at 8.7 $\tau$ U.V. $\lambda_{max}$ 298 n$\mu$, E%185.

Following the above procedure but using 0.25 ml of dimethylsulfate and allowing the reaction to proceed for 15 minutes, there is obtained a mixture containing N-methyl and N,N-dimethyl thienamycin which is separated by column chromatography.

EXAMPLE 20

Preparation of N,N,N-Trimethyl Thienamycin

A suspension of N,N-dimethyl thienamycin (20 mg.), in 10 ml. of tetrahydrofuran is stirred under a nitrogen atmosphere and hexamethyl disilizane (0.2 ml.) and trimethyl chlorosilane (0.1 ml.) are added. The mixture is stirred vigorously at 23° C. for 20 minutes then centrifuged and the supernatant solution is evaporated under reduced pressure. The residual oil is dissolved in THF (1 ml), methyliodide (0.05 ml) is added with vigorous stirring and the mixture is stirred for 30 minutes. Ethyl acetate, 5 ml., and 0.1 N pH 4 phosphate buffer (5 ml) are added, and stirring is continued for 15 minutes at 25° C. The mixture is adjusted to pH 7 and separated. The aqueous layer is concentrated to 1 ml. and applied to a column of XAD-2 resin (20 ml.). Elution with water, followed by 10% tetrahydrofuran, yields a fraction containing N,N,N-trimethyl thienamycin which is freeze-dried to give a solid product.

EXAMPLE 21

N,N-Dimethylthienamycin pivaloyloxymethyl ester

A solution of N,N-dimethylthienamycin (30 mg) and pivaloyloxymethyl bromide 25 mg) in 0.2 ml of hexamethylphosphoramide is stirred at 23° C. for one hour. Ethylacetate (5 ml) is added and the mixture is extracted successively with aqueous sodium bicarbonate solution, water and saturated sodium chloride solution. The organic phase is dried and evaporated to a small volume and chromatographed on 8"×18", 1000$\mu$ silica plate using 5:1 chloroform-methanol solution. The band containing N,N-dimethyl thienamycin pivaloyloxymethyl ester is scrapped off and eluted with ethylacetate.

EXAMPLE 22

N,N-Dimethylthienamycin 3-methyl-2-butenyl ester hydrochloride

To a solution of N,N-dimethyl thienamycin (30 mg) in 0.5 ml of 3-methyl-2-butenyl alcohol containing 3.6 mg of hydrogen chloride is added 21 mg of dicyclohexyl carbodiimide. The solution is stirred at 23° for one hour then filtered from dicyclohexyl urea. The filtrate is evaporated and the residue triturated with ether leaving a solid containing N,N-dimethyl thienamycin 3-methyl-2-butenyl ester hydrochloride.

Following the above procedure but substituting methylthioethanol for 3-methyl-2-butenol there is obtained N,N-dimethyl thienamycin methylthioethyl ester.

EXAMPLE 23

O-Acetyl N,N-Dimethyl thienamycin

N,N-Dimethyl thienamycin (100 mg) is added to a mixture of 0.3 ml of acetic anhydride in 1 ml of pyridine. The mixture is allowed to react at 23° C. for three hours then pumped to dryness under vacuum. The solid residue is dissolved in water and chromatographed on 100 ml of XAD-2 resin. After eluting with water the product is eluted with 10% THF. The fraction containing O-acetyl N,N-dimethyl thienamycin are combined, evaporated and freeze-dried.

EXAMPLE 24

Thienamycin Benzyl Ester

A solution of Thienamycin (47 mg) in 1 ml of water and 1 ml of dioxane is cooled to 0° and adjusted to pH 5 with N sulfuric acid. Phenyldiazomethane (37.2 mg) in 0.5 ml of dioxane is added during 2 minutes while the pH is maintained at 5 by means of an automatic titrator. After an additional 5 minutes, water (5 ml) is added and the mixture is extracted with ether. The aqueous phase is layered with ethylacetate, cooled and adjusted to pH 2.5. The ethylacetate phase is removed and the aqueous phase is adjusted to pH 8 with sodium bicarbonate and extracted twice with ethylacetate. The latter ethylacetate extracts are combined, and dried over anhydrous magnesium sulfate. TLC on silica gel in 1:5 methanol chloroform shows a single ninhydrin positive spot at Rf 0.24. The U.V. of the ethylacetate solution shows a $\lambda_{max}$ at 318 m$\mu$ with an optical density of 250.

EXAMPLE 25

N,N-Dimethyl-O-Sulfo Thienamycin benzyl Ester

To a solution of N,N-dimethyl thienamycin benzyl ester (39 mg) in 0.3 ml of pyridine is added sulfur trioxide-pyridine (17 mg). The mixture is stirred at 25° C. for three hours and the excess pyridine is evaporated under reduced pressure. The residue is taken up in 5 ml of water containing 10 mg of sodium bicarbonate and extracted once with ethylacetate. The aqueous solution is concentrated to 2 ml. and chromatographed on 50 g of XAD-2 resin. The fractions containing N,N-dimethyl-O-sulfo-thienamycin benzyl ester are combined, concentrated and freeze dried.

EXAMPLE 26

N,N-Dimethyl-O-sulfo thienamycin sodium salt

A solution of N,N-dimethyl-o-sulfo thienamycin benzyl ester (24 mg) in 1 ml of water containing 5 mg of sodium bicarbonate is hydrogenated in the presence of 20 mg of palladium oxide at 23° C. 1 atm pressure for 2 hours. The catalyst is removed by filtration and the filtrate is chromatographed on 20 g of XAD-2 resin. The fraction containing N,N-dimethyl-O-sulfo-thienamycin sodium salt are combined, concentrated and freeze-dried.

EXAMPLE 27

O-Formyl-N,N-dimethyl thienamycin benzyl ester

To a solution of N,N-dimethyl thienamycin benzyl ester (100 mg) in 1 ml of pyridine is added a mixture of 100 mg of formic acid and 200 mg of acetic anhydride. The mixture is stirred for 2 hours at 25° C., and the excess reagents are removed under reduced pressure. The residue is taken up in ethylacetate and the product is recovered by thin layer chromatography on silica gel using 1:1 ethylacetate-chloroform solvent.

EXAMPLE 28

O-Formyl N,N-Dimethyl thienamycin

A solution of O-Formyl N,N-dimethylthienamycin benzyl ester (50 mg) in 2 ml of 90% ethanol is hydrogenated in th presence of 50 mg of 10% palladium or charcoal at 23° C. and 1 atm. for 4 hours. The catalyst is removed by filtration The filtrate is evaporated and the residue containing O-Formyl, N,N-dimethyl thienamycin is purified by chromatography on XAD-2 resin.

EXAMPLE 29

Preparation of N-Thioformyl Thienamycin

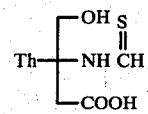

Silylated thienamycin [Th(THS$_3$), from 100 mg thienamycin, Example 4] is dissolved in dichloromethane (9 ml) in a stoppered flask under positive nitrogen pressure. To the magnetically stirred solution is added a solution of triethylamine (60 $\mu$l) in dichloromethane (1 ml). This is followed by the addition of ethyl thioformate (100 $\mu$l). After 1 hour the reaction solution is rapidly added to a stirred solution of pH 4 0.1 N phosphate buffer (20 ml). The mixture is stirred 5 minutes and the pH of the mixture adjusted to 7.0 with 1 N NaOH. The aqueous phase is separated, washed with ethyl acetate (2×20 ml) and cooled in an ice bath. The solution is layered with ethylacetate (15 ml) and the pH of the stirred mixture is adjusted to 3.5 with 1 N phosphoric acid. The organic phase is separated and the buffered aqueous solution washed with ethyl acetate (2×15 ml). The combined ethyl acetate washings are concentrated to half volume and layered with water (10 ml). Solid sodium bicarbonate is added until the pH of the mixture is 7.0. The aqueous phase is separated and lyophilized to give the sodium salt of N-thioformyl thienamycin.

EXAMPLE 30

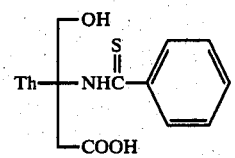

N-(Thiobenzoyl)thienamycin

A solution of 55.8 mg (0.2 mmole) of thienamycin in 18 ml. of dioxane-water (1:1) is treated with 263 mg. (3.1 mmoles) of NaHCO$_3$ and cooled to 0° C. Two 200-$\mu$l portions of a solution of 100 mg of thiobenzoyl chloride in 0.6 ml of dry dioxane are added to the rapidly stirred reaction solution at 15 min. intervals. Each portion of acid chloride solution contains 0.2 mmole of thiobenzoyl chloride. Fifteen minutes after the second addition, the reaction solution is washed with two 8-ml. portions of ether. Ethyl acetate (8 ml) is added to the aqueous phase which is adjusted to pH of 2.2 at 0° C. with rapid stirring using 20% H$_3$PO$_4$. The layers are separated and the aqueous layer is washed with 3 ml. of ethyl acetate. The combined ethyl acetate layers are dried (MgSO₄). After separation of the drying agent, 10 ml of water is added to the ethyl acetate solution and the product is extracted into the aqueous phase by adding 50 mg. (0.62 mmole) of NaHCO₃ with stirring at 0° C. (pH 7.4). The layers are separated and an aqueous phase containing N-(thiobenzoyl)thienamycin sodium salt is obtained, and freeze-dried. Nmr in D₂O: δ 7.3–7.9 characteristic of the

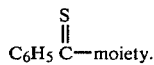

C₆H₅ C—moiety.

EXAMPLE 31

Preparation of N-Methyl thienamycin (I) and N-Benzyl thienamycin (II)

A mixture of N-(thioformyl)thienamycin (100 mg) and neutral Raney nickel (0.5 g) in 100 ml of 90% aqueous ethanol is stirred at 23° C. for two hours. The nickel is removed by filtration and the filtrate is chromatographed on a column (100 ml) of Dowex 50×4, Na⁺ form (400 mesh) resin. The column is eluted with water and the fractions containing N-methyl thienamycin are combined and lyophilized.

Following the procedure of Example 31 except that an equivalent amount of N-(thiobenzoyl)thienamycin is substituted for the N-(thioformyl)thienamycin, there is obtained N-benzyl thienamycin.

 I

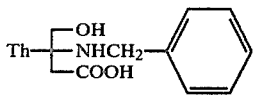 II

EXAMPLE 32

Following the procedures set out in the foregoing Examples and text, the following compounds of the present invention are obtained.

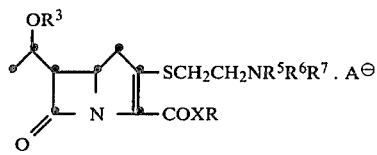

| Compound | X | R³ | R | R⁵ | R⁶ | R⁷ | A |
|---|---|---|---|---|---|---|---|
| 1. | O | H | —CH₂—O—C(=O)—CH₃ | CH₃ | CH₃ | CH₃ | Cl |
| 2. | O | CH₃ | — | CH₃ | CH₃ | CH₃ | — |
| 3. | O | SO₃H | Na | CH₃ | CH₃ | CH₃ | — |
| 4. | O | H | — | CH₃ | CH₃ | C₂H₅ | — |
| 5. | O | H | H | C₂H₅ | CH₃ | — | — |
| 6. | O | H | H | C₂H₅ | C₂H₅ | — | — |
| 7. | O | H | —CH₂—O—CH₂C(CH₃)₃ | —CH₂CH=CH₂ | H | H | Cl |
| 8. | O | H | H | —CH₂CH₂CH₃ | H | — | — |
| 9. | O | H | H | —CHϕ2 | H | — | — |
| 10. | O | H | H | —CHϕ2 | CH₃ | — | — |
| 11. | O | H | H | —C—ϕ3 | CH₃ | — | — |
| 12. | O | H | — | CHϕ2 | CH₃ | CH₃ | — |
| 13. | O | H | —CH₂—CH=CH₂ | —CH₂—CH=CH₂ | H | H | Cl |
| 14. | O | H | —CH₂—C(CH₃)=CH₂ | —CH₂—C(CH₃)=CH₂ | H | H | Cl |
| 15. | O | H | —CH₂CH₂N(C₂H₅)₂ | CH₃ | H | H | H SO₄ |
| 16. | O | —CH₂OCH₃ | p-nitrobenzyl | —CH₂OCH₃ | —CH₂OCH₃ | — | — |
| 17. | S | H | —CH₂CH₂CH₃ | —CH₂CH=CHCH₃ | H | H | Cl |
| 18. | O | H | H | —CH₂CH₂CH=CH₂ | H | — | — |
| 19. | O | H | H | —CH₂—C₆H₅ | H | — | — |
| 20. | O | —C(=O)OCH₃ | H | —CH₂-(pyrrole NH) | H | — | — |
| 21. | O | H | H | —CH₂CH₂CH₂CH₂— | — | — | — |
| 22. | O | H | —CH₂CH₂N—(CH₃)₂ | —CH₂CH₂—N—(CH₃)₃ | H | H | H PO₄ |
| 23. | O | H | H | —CH₂—C(=O)—CH₃ | H | — | — |
| 24. | O | H | H | —CH₂CH₂(OCH₃)₂ | H | — | — |
| 25. | O | H | H | —CH₂—C≡CH | H | — | — |
| 26. | O | H | H | —CH₂CH₂O—CH₂CH₂— | H | — | — |
| 27. | O | H | —CH₂C(=O)ϕ | —CH₂C(=O)ϕ | CH₃ | — | — |
| 28. | O | H | CH₂S—CH₃ | —CH₂SCH₃ | —CH₂SCH₃ | — | — |

-continued

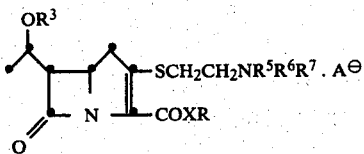

| Compound | X | R³ | R | R⁵ | R⁶ | R⁷ | A |
|---|---|---|---|---|---|---|---|
| 29. | O | H | —CH₂—O—C(=O)C(CH₃)₃ | —CH₂—O—C(=O)C(CH₃)₃ | H | — | — |
| 30. | O | Si(CH₃)₃ | Si(CH₃)₃ | —CH₂CH₂C≡N | H | — | — |
| 31. | O | H | H | —CH₂CH₂—C(=O)—OCH₃ | H | — | — |
| 32. | O | H | H | 2,4-dinitrophenyl | H | — | — |
| 33. | O | —C(=O)—CH₂NH₂ | H | —C₂H₅ | —C₂H₅ | H | CH₃COO |
| 34. | O | H | H | —CH₂-cyclopropyl | —CH₂-cyclopropyl | — | — |
| 35. | O | H | H | —CH(CH₃)₂ | H | — | — |
| 36. | O | H | H | —CH₂CH₂CH₂CH₃ | H | — | — |
| 37. | O | H | H | —CH₂CH(CH₃)—CH₃ | H | — | — |
| 38. | O | H | H | —CH(CH₃)CH₂CH₃ | H | — | — |
| 39. | O | H | H | —CH₂CH₂CH₂CH₂CH₃ | H | — | — |
| 40. | O | H | H | —CH(CH₃)—CH₂CH₂CH₃ | H | — | — |
| 41. | O | H | H | —CH₂—CH(CH₃)—CH₂CH₃ | H | — | — |
| 42. | O | H | H | —CH₂CH₂CH(CH₃)—CH₃ | H | — | — |
| 43. | O | H | H | —CH(CH₃)—CH(CH₃)—CH₃ | H | — | — |
| 44. | O | H | H | —CH₂—C(CH₃)₃ | H | — | — |
| 45. | O | H | H | —CH₂CH₂CH₂CH₂CH₂CH₃ | H | — | — |
| 46. | O | H | H | —CH(CH₃)CH₂CH(CH₃)₂ | H | — | — |
| 47. | O | H | H | —CH₂CH=CH₂ | H | — | — |
| 48. | O | H | H | —CH₂CH(CH₃)—CH₃ | H | — | — |
| 49. | O | H | H | —CH(CH₂)—CH=CH₂ | H | — | — |
| 50. | O | H | H | —CH₂CH=CH—CH₃ | H | — | — |
| 51. | O | H | H | —CH(CH₃)—CH₂—CH=CH₂ | H | — | — |
| 52. | O | H | H | —CH(C₂H₅)—CH=CH₂ | H | — | — |
| 53. | O | H | H | —CH₂—CH=CH—CH₂CH₃ | H | — | — |
| 54. | O | H | H | —CH₂CH=CH—CH₂CH₂CH₃ | H | — | — |
| 55. | O | H | H | —CH₂—C(CH₃)=CH—CH₂CH₃ | H | — | — |
| 56. | O | H | H | —CH₂—CH—CH=CH—CH₃ | H | — | — |

-continued

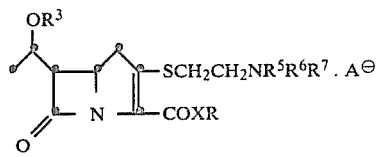

| Compound | X | R³ | R | R⁵ | R⁶ | R⁷ | A' |
|---|---|---|---|---|---|---|---|
| 57. | O | H | H | CH₂CH=CH—CH(CH₃)— | H | — | — |
| 58. | O | H | H | cyclopropyl | H | — | — |
| 59. | O | H | H | cyclopentenyl | H | — | — |
| 60. | O | H | H | —CH₂CH₂—(cyclohexenyl) | H | — | — |
| 61. | O | H | H | —CH₂—phenyl | H | — | — |
| 62. | O | H | H | —CH₂—phenyl | H | — | — |
| 63. | O | H | H | —CH₂—CH=cyclopentylidene | H | — | — |
| 64. | O | H | H | furyl | H | — | — |
| 65. | O | H | H | thienyl | H | — | — |
| 66. | O | H | H | —CH₂—furyl | H | — | — |
| 67. | O | H | H | —CH₂—CH=CH—φ | H | — | — |
| 68. | O | H | H | —CH₂—C₆H₄—OCH₃ | H | — | — |
| 69. | O | H | H | —CH₃ | —CH₂CH=CH₂ with CH₃ | — | — |
| 70. | O | H | H | —CH₃ | —CH₂CH=CH—CH₃ | — | — |
| 71. | O | H | H | —CH₃ | —CH(CH₃)—CH=CH₂ | — | — |
| 72. | O | H | H | —CH₃ | —CH=CH—CH₂CH₃ | — | — |
| 73. | O | H | H | —CH₃ | —CH₂—C(CH₃)=CH—CH₃ | — | — |
| 74. | O | H | H | —CH₃ | —CH₂—CH=CH—CH(CH₃)— | — | — |
| 75. | O | H | H | —CH₃ | cyclopentenyl | — | — |
| 76. | O | H | H | —CH₃ | —CH₂—cyclohexadienyl | — | — |

-continued $$\begin{array}{c} OR^3 \\ \diagup \\ \text{[β-lactam core]} \\ \text{—SCH}_2\text{CH}_2\text{NR}^5\text{R}^6\text{R}^7 \cdot A^\ominus \\ \text{—COXR} \end{array}$$

| Compound | X | R³ | R | R⁵ | R⁶ | R⁷ | A |
|---|---|---|---|---|---|---|---|
| 77. | O | H | H | —CH₃ | —CH₂—C₆H₄—OCH₃ | — | — |
| 78. | O | H | H | —CH₃ | —CH₂—(2-thienyl) | — | — |
| 79. | O | H | H | —CH₃ | —CH₂—CH=CH—φ | — | — |

EXAMPLE 33

Preparation of Pharmaceutical Compositions

One such unit dosage form consists in mixing 120 mg. of N,N,N-trimethyl-thienamycin chloride with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| N,N,N-trimethyl-thienamycin chloride | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C., and screened again through No. 16 screens. The balance of the cornstarch and the magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| N,N,N-trimethyl-thienamycin chloride | 500 mg. |
| Diluent: Sterile Water for Injection | 2 cc. |
| OPTHALMIC SOLUTION | |
| N,N,N-trimethyl-thienamycin chloride | 100 mg. |
| Hydroxypropylmethyl Cellulose | 5 mg. |
| Sterile Water to | 1 ml. |
| OTIC SOLUTION | |
| N,N,N-trimethyl-thienamycin chloride | 100 mg. |
| Benzalkonium Chloride | 0.1 mg. |
| Sterile Water to | 1 ml. |
| TOPICAL OINTMENT | |
| N,N,N-trimethyl-thienamycin chloride | 100 mg. |
| Polyethylene Glycol 4000 U.S.P. | 400 mg. |

| | PER TABLET |
|---|---|
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin, and kanamycin, or with other therapeutic agents such as probenecid.

What is claimed is:

1. A compound having the structural formulae:

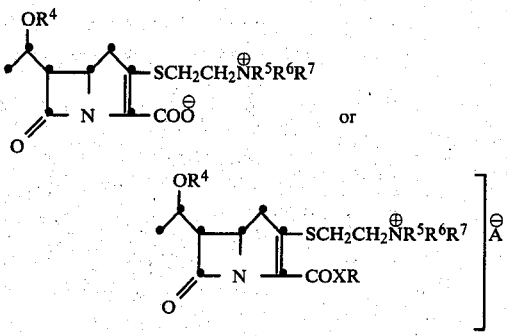

wherein R⁴ is a member selected from the group consisting of hydrogen, loweralkyl, sulfo, loweralkoxyloweralkyl, loweralkoxycarbonyl, loweralkanoyl and aminoloweralkanoyl; R⁵, R⁶, and R⁷ are independently selected from the group consisting of hydrogen (not all of R⁵, R⁶ and R⁷ are hydrogen at the same time), CH₃, CH₂CH₃, CH₂CH=CH₂, CH₂CH₂CH₃, CH₂(C₆H₅), CH(C₆H₅)₂, C(C₆H₅)₃, $CH_2\underset{\underset{CH_3}{|}}{C}=CH_2$, $CH_2OCH_3$, $CH_2CH=CH—CH_3$, $CH_2CH_2CH=CH_2$, $CH_2\overset{O}{\overset{\|}{C}}CH_3$, $CH_2CH_2(OCH_3)_2$, $CH_2—C\equiv CH$, $CH_2\overset{O}{\overset{\|}{C}}(C_6H_5)$, $CH_2SCH_3$, -continued

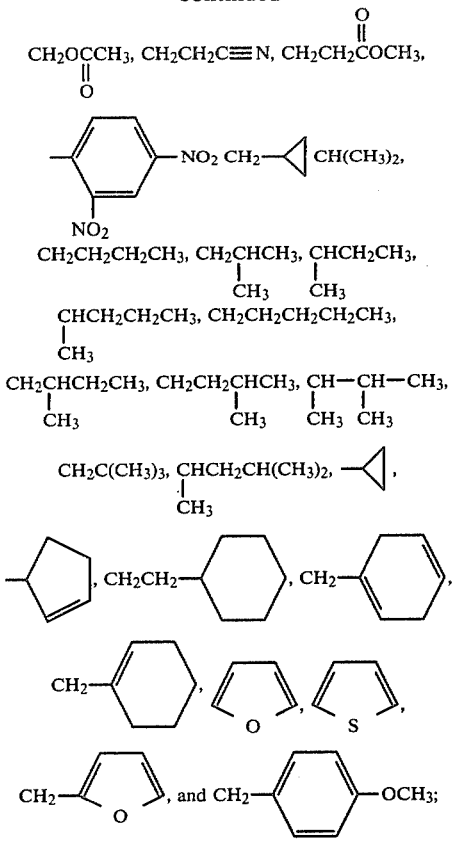

X of the group, —COXR is O or S; R is selected from the group consisting of hydrogen, methyl, t-butyl, phenacyl, p-bromophenacyl; pivaloyloxymethyl, 2,2,2-trichloroethyl, allyl, 3-methyl-2-butenyl, 2-methyl-2-propenyl, benzyl, benzylhydryl, p-t-butylbenzyl, phthalidyl, phenyl, 5-indanyl, acetylthiomethyl, acetoxymethyl, propionyloxymethyl, methallyl, 3-butenyl, 4-pentenyl, 2-butenylacetoxyacetylmethyl, pivaloylacetylmethyl, diethylamino, dimethylaminoethyl, methoxymethyl, p-acetoxybenzyl, p-pivaloylbenzyl, p-isopropoxybenzyl, 5-indanylmethyl, benzyloxymethyl, methylthioethyl, dimethylaminoacetoxymethyl, crotonolacton-3-yl, acetamidomethyl, acetylthioethyl, pivaloylthiomethyl, methylthiomethyl; and A is a pharmaceutically acceptable anion.

2. A compound according to claim 1 wherein $R^4$ is hydrogen, X is oxygen, and R is hydrogen, and the pharmaceutically acceptable salts thereof.

3. A compound according to claim 2 wherein $R^5$, $R^6$ and $R^7$ are hydrogen or loweralkyl having 1–6 carbon atoms.

4. The compound according to claim 3 having the structure:

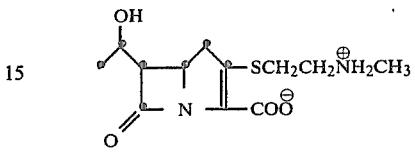

5. The compound according to claim 3 having the structure:

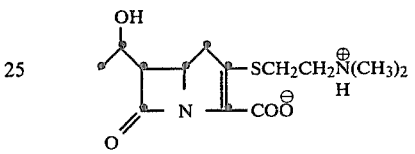

6. A compound according to claim 3 having the structure:

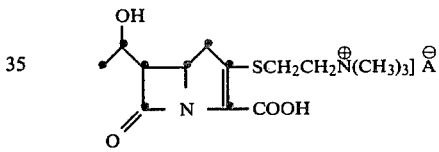

wherein A is a pharmaceutically acceptable anion.

7. The compound according to claim 6 wherein A is chloro.

8. An antibiotic pharmaceutical composition consisting essentially of a therapeutically effective amount of a compound according to claim 1 and a pharmaceutical carrier therefor.

* * * * *